United States Patent
Lim et al.

(10) Patent No.: US 11,191,853 B2
(45) Date of Patent: Dec. 7, 2021

(54) POST-SURGICAL IMAGING MARKER

(71) Applicant: THE JOHNS HOPKINS UNIVERSITY, Baltimore, MD (US)

(72) Inventors: Michael Lim, Baltimore, MD (US); Henry Brem, Baltimore, MD (US); Betty Tyler, Baltimore, MD (US); Jason Liauw, Baltimore, MD (US); Sheng-Fu Lo, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 15/503,887

(22) PCT Filed: Aug. 14, 2015

(86) PCT No.: PCT/US2015/045194
§ 371 (c)(1),
(2) Date: Feb. 14, 2017

(87) PCT Pub. No.: WO2016/025786
PCT Pub. Date: Feb. 18, 2016

(65) Prior Publication Data
US 2017/0274102 A1    Sep. 28, 2017

Related U.S. Application Data

(60) Provisional application No. 62/037,981, filed on Aug. 15, 2014.

(51) Int. Cl.
*A61K 49/18* (2006.01)
*A61K 49/10* (2006.01)
*A61K 49/12* (2006.01)

(52) U.S. Cl.
CPC ........ *A61K 49/1896* (2013.01); *A61K 49/101* (2013.01); *A61K 49/12* (2013.01); *A61K 49/1803* (2013.01); *A61K 49/1827* (2013.01)

(58) Field of Classification Search
CPC .. A61K 49/1896; A61K 49/101; A61K 49/12; A61K 49/1803; A61K 49/1887; A61B 5/05; A61B 5/0515; A61B 5/06; A61B 17/50; A61L 2400/18
See application file for complete search history.

(56) References Cited

U.S. PATENT DOCUMENTS

| | | |
|---|---|---|
| 1,683,347 A | 9/1928 | Gray |
| 1,698,049 A | 1/1929 | Clarke |
| 1,880,560 A | 10/1932 | Webber |
| 1,880,808 A | 10/1932 | Clarke |
| 1,984,147 A | 12/1934 | Malm |
| 2,129,052 A | 9/1938 | Fordyce |
| 3,475,407 A | 10/1969 | Upjohn |
| 3,509,127 A | 4/1970 | Upjohn |
| 3,513,155 A | 5/1970 | Upjohn |
| 3,544,551 A | 12/1970 | Upjohn |
| 3,617,201 A | 11/1971 | Berni et al. |
| 5,514,379 A * | 5/1996 | Weissleder ........... A61K 9/1658 424/426 |
| 5,603,955 A * | 2/1997 | Gehrke .................. A61K 9/205 424/484 |
| 5,837,752 A * | 11/1998 | Shastri ................... A61L 27/26 523/116 |
| 6,083,524 A * | 7/2000 | Sawhney ............ A61L 24/0042 424/426 |
| 2004/0047835 A1* | 3/2004 | Bianco .................... A61K 31/00 424/78.17 |
| 2004/0047865 A1* | 3/2004 | Warner ................ A61K 47/643 424/178.1 |
| 2004/0267234 A1* | 12/2004 | Heart .................. A61M 31/002 604/500 |
| 2005/0079138 A1* | 4/2005 | Chickering, III ...... A61K 9/145 424/46 |
| 2005/0255045 A1 | 11/2005 | Woltering |
| 2009/0053141 A1 | 2/2009 | Sulzer |
| 2012/0189551 A1 | 7/2012 | Frank et al. |
| 2012/0219496 A1 | 8/2012 | Tsourkas et al. |
| 2013/0289533 A1* | 10/2013 | Duering ................ A61L 29/126 604/529 |
| 2013/0324837 A1* | 12/2013 | Meyer ................... A61L 29/085 600/417 |

FOREIGN PATENT DOCUMENTS

| | | |
|---|---|---|
| CA | 2196304 A1 | 2/2011 |
| WO | 199832675 A2 | 7/1998 |

OTHER PUBLICATIONS

Weingart, J. et al., Phase I trial of polifeprosan 20 with carmustine 3 implant plus continuous infusion of intravenous 06-benzylguanine in adults with recurrent malignant glioma: new approaches to brain tumor therapy CNS consortium trial, Journal of Clinical Oncology, 2007, vol. 25, No. 4, pp. 399-404.
Weingart, J., et al., Phase 1 trial of polifeprosan 20 with carmustine implant plus continuous infusion of intravenous 06-benzylguanine in adults with recurrent malignant glioma: new approaches to brain tumor therapy CNS consortium trial, Journal of Clinical Oncology, 2007, vol. 25, No. 4, pp. 399-404.
International Search Report issued in corresponding International Application No. PCT/US2015/045194, dated Oct. 29, 2015, 4 pages.
Written Opinion of the International Searching Authority issued in corresponding International Application No. PCT/US2015/045194, dated Oct. 29, 2015, 7 pages.

* cited by examiner

*Primary Examiner* — Micah Paul Young
(74) *Attorney, Agent, or Firm* — Mintz Levin Cohn Ferris Glovsky and Popeo, P.C.; Peter F. Corless

(57) ABSTRACT

A marker for imaging includes a bio-dissolvable material and a contrast agent configured to provide contrast during an imaging procedure. A method can include forming a marker for imaging from a bio-dissolvable material and impregnating the bio-dissolvable material with a contrast agent. A method can include implanting a bio-dissolvable marker for imaging into a patient.

21 Claims, 2 Drawing Sheets

POST-SURGICAL IMAGING MARKER

RELATED APPLICATIONS

This application is the U.S. national stage pursuant to 35 U.S.C. § 371, of International Application Ser. No. PCT/US2015/045194, filed Aug. 14, 2015 and published in English on Feb. 18, 2016 as publication WO2016/025786 A1, which claims the benefit of priority under 35 U.S.C. § 119(e) to U.S. Provisional Application No. 62/037,981, filed Aug. 15, 2014, which are incorporated herein by reference in their entirety.

BACKGROUND

1. Field

The present disclosure relates to markers for imaging for medical procedures, more specifically to markers for magnetic resonance imaging.

2. Description of Related Art

Marking critical areas of interest intra-operatively may improve the efficacy of therapies given post-operatively such as in the case of stereotactic radiosurgery. Conventional markers include metal beads and the like. Such traditional markers stay in the anatomy of the patient until surgically removed.

Such conventional methods and systems have generally been considered satisfactory for their intended purpose. However, there is still a need in the art for improved markers. The present disclosure provides a solution for this need.

SUMMARY

In at least one aspect of this disclosure, a marker for imaging includes a bio-dissolvable material and a contrast agent configured to provide contrast during an imaging procedure. The bio-dissolvable material can include a polymer.

The polymer can include polifeprosan or any other suitable polymer. The contrast agent can include Gadolinium or any other suitable contrast agent. The marker can be wafer shaped or any other suitable shape.

In at least one aspect of this disclosure, a method can include forming a marker for imaging from a bio-dissolvable material and impregnating the bio-dissolvable material with a contrast agent. The method can further include shaping the marker into a wafer shape.

In at least one aspect of this disclosure, a method can include implanting a bio-dissolvable marker for imaging into a patient.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
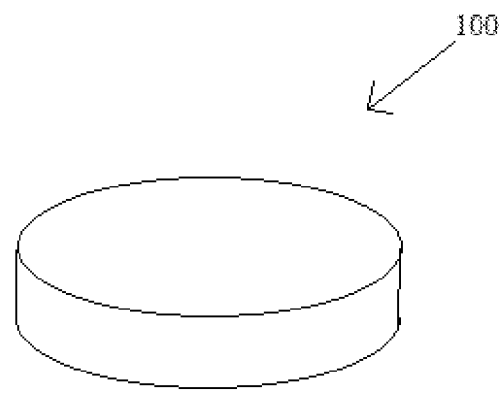
FIG. 1 is a perspective view of an embodiment of a marker in accordance with this disclosure, shown including a cylindrical wafer shape.

The present invention relates to a marker for imaging includes a bio-dissolvable material and a contrast agent configured to provide contrast during an imaging procedure. The bio-dissolvable material can include a polymer.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

Definitions

As used herein, the term "hydrogel" is a type of "gel," and refers to a water-swellable polymeric matrix, consisting of a three-dimensional network of macromolecules (e.g., hydrophilic polymers, hydrophobic polymers, blends thereof) held together by covalent or non-covalent crosslinks that can absorb a substantial amount of water to form an elastic gel. The polymeric matrix may be formed of any suitable synthetic or naturally occurring polymer material. As used herein, the term "gel" refers to a solid three-dimensional network that spans the volume of a liquid medium and ensnares it through surface tension effects. This internal network structure may result from physical bonds (physical gels) or chemical bonds (chemical gels), as well as crystallites or other junctions that remain intact within the extending fluid. Virtually any fluid can be used as an extender including water (hydrogels), oil, and air (aerogel). Both by weight and volume, gels are mostly fluid in composition and thus exhibit densities similar to those of their constituent liquids. A hydrogel is a type of gel that uses water as a liquid medium.

The definitions of "hydrophobic" and "hydrophilic" polymers are based on the amount of water vapor absorbed by polymers at 100% relative humidity. According to this classification, hydrophobic polymers absorb only up to 1% water at 100% relative humidity ("rh"), while moderately hydrophilic polymers absorb 1-10% % water, hydrophilic polymers are capable of absorbing more than 10% of water, and hygroscopic polymers absorb more than 20% of water. A "water-swellable" polymer is one that absorbs an amount of water greater than at least 50% of its own weight, upon immersion in an aqueous medium.

The term "bio-dissolvable materials" refers to a material which over time is partially or fully absorbed by the body. Such materials can include gels and/or hydrogels, polymers, or other suitable materials. Such materials can be synthetic, naturally occurring, or a blends or composites thereof. An equivalent term for purposes of this invention is "biodegradable" materials.

The term "crosslinked" herein refers to a composition containing intramolecular and/or intermolecular crosslinks, whether arising through covalent or noncovalent bonding. "Noncovalent" bonding includes both hydrogen bonding and electrostatic (ionic) bonding. The term "polymer" includes linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da. Polymers and oligomers may be naturally occurring or obtained from synthetic sources.

Marker

The marker of the present invention can include a polymer. In certain aspects, the polymer can be any suitable polymer, including any suitable bio-dissolvable polymer. In one embodiment, the polymer is polifeprosan. The polymer can also be configured to form a gel or hydrogel.

In a particular embodiment, the imaging marker of the invention comprises commercially available GLIADEL Wafer, which is an implant for intracranial use that comprises carmustine, a nitrosourea alkylating agent, and polifeprosan, a biodegradable copolymer used to control the release of carmustine. GLIADEL is a sterile, off-white to pale yellow wafer approximately 1.45 cm in diameter and 1 mm thick. Each wafer contains 7.7 mg of carmustine [1,3-bis (2-chloroethyl)-1-nitrosourea, or BCNU] and 192.3 mg of a biodegradable polyanhydride copolymer. The copolymer, polifeprosan 20, consists of poly [bis (p-carboxyphenoxy)] propane and sebacic acid in a 20:80 molar ratio. Carmustine is homogeneously distributed in the copolymer matrix. The invention also contemplates any suitable variations or derivatives of GLIADEL.

In certain embodiments, the polymers used herein can form gels or hydrogels that will be suitable for use in the markers of the invention.

The gel/hydrogel of the invention can include any type of suitable hydrogel component. The invention contemplates gel components that include any suitable gel component, including any suitable hydrogel component known in the art. The gel and/or hydrogels can be formed of any suitable synthetic or naturally-occurring materials.

For example, the polymer component of the gels and/or hydrogels can comprise a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000.

The cellulose esters and comprise a mixture of cellulose and cellulose ester monomer units; for example, commercially available cellulose acetate butyrate contains cellulose acetate monomer units as well as cellulose butyrate monomer units and unesterified cellulose units.

The gels/hydrogels of the invention may also be comprised of other water-swellable polymers, such as acrylate polymers, which are generally formed from acrylic acid, methacrylic acid, methyl acrylate, ethyl acrylate, methyl methacrylate, ethyl methacrylate, and/or other vinyl monomers. Suitable acrylate polymers are those copolymers available under the tradename "Eudragit" from Rohm Pharma (Germany), as indicated supra. The Eudragit series E, L, S, RL, RS and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L-30D-55 and Eudragit L-100-55 (the latter copolymer is a spray-dried form of Eudragit L-30D-55 that can be reconstituted with water). The molecular weight of the Eudragit L-30D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-30D-55, L-100-55, L-100, and S-100 can be replaced with other acceptable polymers having similar pH-dependent solubility characteristics.

The herein-described gel/hydrogel marker compositions may be modified so as to contain an active agent and thereby act as an active agent delivery system when applied to a body surface (e.g., a site of tissue repair) in active agent-transmitting relation thereto. The release of active agents "loaded" into the present hydrogel compositions of the invention typically involves both absorption of water and desorption of the agent via a swelling-controlled diffusion mechanism. Active agent-containing hydrogel compositions may be employed, by way of example, in transdermal drug delivery systems, in wound dressings, in topical pharmaceutical formulations, in implanted drug delivery systems, in oral dosage forms, and the like.

Suitable active agents that may be incorporated into the present hydrogel compositions and delivered systemically (e.g., with a transdermal, oral, or other dosage form suitable for systemic administration of a drug) include, but are not limited to: analeptic agents; analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, antianginal agents, central nervous system (CNS) agents, beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids, including progestogens, estrogens, corticosteroids, androgens and anabolic agents; smoking cessation agents; sympathomimetics; tranquilizers; and vasodilators including general coronary, peripheral and cerebral. Specific active agents with which the present adhesive compositions are useful include, without limitation, anabasine, capsaicin, isosorbide dinitrate, aminostigmine, nitroglycerine, verapamil, propranolol, silabolin, foridone, clonidine, cytisine, phenazepam, nifedipine, fluacizin, and salbutamol.

Bacteriostatic and bactericidal agents are also contemplated to be included in the markers of the invention. Suitable bacteriostatic and bactericidal agents include, by way of example: halogen compounds such as iodine, iodopovidone complexes (i.e., complexes of PVP and iodine, also referred to as "povidine" and available under the tradename Betadine® from Purdue Frederick), iodide salts, chloramine, chlorohexidine, and sodium hypochlorite; silver and silver-containing compounds such as sulfadiazine, silver protein acetyltannate, silver nitrate, silver acetate, silver lactate, silver sulfate and silver chloride; organotin compounds such as tri-n-butyltin benzoate; zinc and zinc salts; oxidants, such as hydrogen peroxide and potassium permanganate; aryl mercury compounds, such as phenylmercury borate or merbromin; alkyl mercury compounds, such as thiomersal; phenols, such as thymol, o-phenyl phenol, 2-benzyl-4-chlorophenol, hexachlorophen and hexylresorcinol; and organic nitrogen compounds such as 8-hydroxyquinoline, chlorquinaldol, clioquinol, ethacridine, hexetidine, chlorhexedine, and ambazone.

Antibiotic agents may also be incorporated into the markers of the invention. Suitable antibiotic agents include, but are not limited to, antibiotics of the lincomycin family (referring to a class of antibiotic agents originally recovered from *streptomyces lincolnensis*), antibiotics of the tetracycline family (referring to a class of antibiotic agents originally recovered from *streptomyces aureofaciens*), and sulfur-based antibiotics, i.e., sulfonamides. Exemplary antibiotics of the lincomycin family include lincomycin, clindamycin, related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself, chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium.

Pain relieving agents may also be added to or integrated in the markers of the invention. Suitable pain relieving agents are local anesthetics, including, but not limited to, acetamidoeugenol, alfadolone acetate, alfaxalone, amucaine, amolanone, amylocaine, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, .beta.-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and combinations thereof. Tetracaine, lidocaine and prilocaine are referred pain relieving agents herein.

Other topical agents that may be delivered using the present marker compositions as drug delivery systems include the following: antifungal agents such as undecylenic acid, tolnaftate, miconazole, griseofulvine, ketoconazole, ciclopirox, clotrimazole and chloroxylenol; keratolytic agents, such as salicylic acid, lactic acid and urea; vessicants such as cantharidin; anti-acne agents such as organic peroxides (e.g., benzoyl peroxide), retinoids (e.g., retinoic acid, adapalene, and tazarotene), sulfonamides (e.g., sodium sulfacetamide), resorcinol, corticosteroids (e.g., triamcinolone), alpha-hydroxy acids (e.g., lactic acid and glycolic acid), alpha-keto acids (e.g., glyoxylic acid), and antibacterial agents specifically indicated for the treatment of acne, including azelaic acid, clindamycin, erythromycin, meclocycline, minocycline, nadifloxacin, cephalexin, doxycycline, and ofloxacin; skin-lightening and bleaching agents, such as hydroquinone, kojic acid, glycolic acid and other alpha-hydroxy acids, artocarpin, and certain organic peroxides; agents for treating warts, including salicylic acid, imiquimod, dinitrochlorobenzene, dibutyl squaric acid, podophyllin, podophyllotoxin, cantharidin, trichloroacetic acid, bleomycin, cidofovir, adefovir, and analogs thereof; and anti-inflammatory agents such as corticosteroids and nonsteroidal anti-inflammatory drugs (NSAIDs), where the NSAIDS include ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, and tiaprofenic acid.

For wound dressings, suitable active agents are those useful for the treatment of wounds, and include, but are not limited to bacteriostatic and bactericidal compounds, antibiotic agents, pain relieving agents, vasodilators, tissue-healing enhancing agents, amino acids, proteins, proteolytic enzymes, cytokines, and polypeptide growth factors.

In certain other embodiments, the marker compositions of the invention comprising a gel (e.g., a hydrogel component) may also comprise additional optional additive components. Such components are known in the art and can include, for example, fillers, preservatives, pH regulators, softeners, thickeners, pigments, dyes, refractive particles, stabilizers, toughening agents, detackifiers, pharmaceutical agents (e.g., antibiotics, angiogenesis promoters, antifungal agents, immunosuppressing agents, antibodies, and the like), and permeation enhancers. These additives, and amounts thereof, are selected in such a way that they do not significantly interfere with the desired chemical and physical properties of the hydrogel composition.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon.

The compositions can also include one or more preservatives. Preservatives include, by way of example, p-chlorom-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

The compositions may also include pH regulating compounds. Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of an individual's body surface.

The compositions may also include suitable softening agents. Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

The compositions may also include thickening agents. Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

In various other embodiments, the marker materials of the invention can be based on hyaluronic acid (HA) as the hydrogel material. HA is a non-sulfated, linear polysaccharide with repeating disaccharide units which form the hydrogel component. HA is also a non-immunogenic, native component of the extracellular matrix in human tissues, and widely used as a dermal filler in aesthetic and reconstructive procedures.

Breakdown of HA is facilitated by native hyaluronidases whose expression is increased in areas of tissue damage and inflammation. Importantly, studies have shown that small HA degradation fragments of 3-10 disaccharide units are potent regulators of endothelial cell proliferation, migration, tubule formation, and angiogenesis. These biological functions of HA are thought to be mediated via CD44 in a pathway involving Ras and PKC. Blockade of CD44/HA interactions using anti-CD44 antibodies reduced proliferation and migration of human microvascular endothelial cells in vitro. HA hydrogels have been investigated as potential matrices for cell delivery in a variety of models of cell and tissue injury. These hydrogels can serve as a protective and supporting scaffold for cells and can also reduce scarring. Thus, it is believed HA has a critical role in enhancing tissue regeneration by promoting cell infiltration and promoting angiogenesis.

First, the material has three-dimensional integrity and a consistency similar to that of native fat tissue. This renders it suitable for off-the-shelf restoration of missing soft tissue volume. Second, the material preferably may be deposited with a plurality of flexible nanofibers that can serve as substrates for migration of adipocytes and endothelial progenitors. Third, the material has sufficient porosity to allow these precursor cells to rapidly infiltrate and integrate into the scaffold rather than forming a fibrous capsule around it. Fourth, the HA hydrogel component provides compressibility and volumetric expansion while also providing important angiogenic cues. Fifth, the nanofiber and hydrogel components are biodegradable allowing them to be replaced by regenerated soft tissue. Sixth, all component materials have strong safety track records in numerous FDA-approved devices, potentially reducing regulatory hurdles for clinical translation.

The marker compositions of the invention can also include tissue-repairing agents, such as, a number of growth factors, including epidermal growth factor (EDF), PDGF, and nerve growth factors (NGF's). For example, the compositions may include EGF. Epidermal Growth Factor (EGF) was discovered after the observation that cutaneous wounds in laboratory mice seemed to heal more rapidly when the mice were allowed to lick them. This was not simply due to some antiseptic agent in saliva (such as lysozyme). A specific growth factor, now known as EGF, was shown to be responsible. EGF is identical to urogastrone, and has angiogenic properties. Transforming growth factor-alpha (TGF-.alpha.) is very similar, binding to the same receptor and is even more effective in stimulating epithelial cell regeneration (epithelisation).

Thus, hydrogels of the present invention comprising EGF/TGF may advantageously be used in the acceleration of wound healing at the surgical site being monitored, reduction in keloid scar formation (especially for burns), skin engraftment dressings, and the treatment of chronic leg ulcers.

Tissue-repairing agents useful in the present invention include a number of growth factors, including epidermal growth factor (EDF), PDGF, and nerve growth factors (NGF's). Generally, growth-promoting hormones will affect between one and four tissues. Many of the products developed from such proteins are targeted towards wound repairs of one kind or another, although there are other indications. Some of the most important tissue growth factors are described further below.

The marker compositions of the invention may also include one or more growth factors that may be useful in the tissue repair methods and other applications of the invention.

For example, the invention contemplates include PDGF in the compositions of the invention. Platelet-Derived Growth Factor (PDGF) is a mitogen for almost all mesenchymally-derived cells, i.e. blood, muscle, bone, cartilage, and connective tissue cells. It is a dimeric glycoprotein existing as AA or BB homodimers, or as the AB heterodimer. As with many growth factors, PDGF is now considered to be a member of a larger family of factors. In addition to PDGF, this family includes the homodimeric factors vascular endothelial growth factor (VEGF) and placental growth factor (PlGF), VEGF/PlGF heterodimers, and connective tissue growth factor (CTGF), a PDGF-like factor secreted by human vascular endothelial cells and fibroblasts. Along with NGF, TGF-.beta. and glycoprotein hormones such as human chorionic gonadotropic hormone (hCG), PDGF is now classified as a member of the cysteine-knot growth factor superfamily. All of these factors may be used in conjunction with hydrogels of the present invention.

PDGF is produced by platelets and released in the course of blood clotting. It is just one of the growth factors that derive from these cells. PDGF attracts fibroblasts and white blood cells to the site of the injury, as well as stimulating the growth of replacement connective tissue (mainly fibroblasts and smooth muscle cells). It stimulates cell division in various cells, including those that produce collagen, so encouraging angiogenesis. It also stimulates mitogenesis, vasoconstriction, chemotaxis, enzyme activity and calcium mobilization.

Blood platelet derived growth factors may be used to restore bone and soft tissue regrowth during certain treatments using the compositions of the invention and to accelerate the healing process of chronic and acute wounds. Accordingly, hydrogel/nanostructure compositions of the present invention may advantageously comprise a platelet derived growth factor cocktail.

The marker compositions of the present invention may be used in gene therapy for local delivery of the PDGF gene, for example. Plasmid DNA encoding PDGF is incorporated into the hydrogel matrix and granulation tissue fibroblasts, which originate in viable tissue surrounding the wound, proliferate and migrate into the matrix, acting as targets for plasmid gene transfer and expression.

The marker compositions of the invention may also include VEGF to promote angiogenesis. Vascular Endothelial Growth Factor (VEGF—also known as vascular permeability factor) is another vascular growth factor, and is a multifunctional angiogenic cytokine. It contributes to angiogenesis (blood vessel growth) both indirectly and directly by stimulating proliferation of endothelial cells at the microvessel level, causing them to migrate and to alter their generic expression. VEGF also makes theses endothelial cells hyperpermeable, causing them to release plasma proteins outside the vascular space, which causes changes in the area, contributing to angiogenesis.

The compositions of the invention may also include FGF. Fibroblast Growth Factor (FGF) is actually a family of at least 19 14 18 kD peptides belonging to the heparin-binding growth factors family, and are mitogenic for cultured fibroblasts and vascular endothelial cells. They are also angiogenic in vivo and this angiogenicity is enhanced by TNF. FGF's may be used in a similar manner to EGF. bFGF, also known as FGF-2, is involved in controlling human megakaryocytopoiesis and FGFs have been shown to be effective in stimulating endothelial cell formation, and in assisting in connective tissue repair.

The marker compositions may also comprise Keratinocyte Growth Factor (KGF), also known as FGF-7, for use in wound healing and other disorders involving epithelial cell destruction.

The markers may also include Transforming Growth Factors (TGFs), which have the ability to transform various cell lines, and can confer, for example, the ability to grow in culture for more than a limited number of generations, growth in multiple layers rather than monolayers, and the acquisition of an abnormal karyotype. There are at least five members of the TGF family, the two most widely studied being TGF-alpha and TGF-beta. The former is mitogenic for fibroblasts and endothelial cells, angiogenic, and promotes bone resorption. Compositions also may include TGF. TGF-beta is a general mediator of cell regulation, a powerful inhibitor of cell growth, and inhibits the proliferation of many cell types. TGF-beta can antagonise the mitogenic effects of other peptide growth factors, and can also inhibit the growth of many tumour cell lines. TGF-beta also has angiogenic effects, and promotes collagen formation in fibroblasts. Indications for hydrogels of the present invention include chronic skin ulcers, such as neurotrophic foot ulcers in diabetic patients. Other areas include wound healing, bone repair and immunosuppressive diseases.

The markers compositions of the present invention may be used to carry suitable cells, for example. These may be incorporated into the gel just prior to application to a wound, or other suitable area, to maximize efficacy. Suitable cells include autologous fibroblasts and keratinocytes, which are mainly responsible for dermis and epidermis formation. Separate gels each comprising one cell type may be applied consecutively or together, or one gel may comprise both cell types, but this is generally less preferred.

The marker compositions of the present invention may usefully comprise collagen, for example. Although collagen, in this form, is unlikely to serve a useful structural function, it primarily serves as a sacrificial protein where proteolytic activity is undesirably high, thereby helping to prevent maceration of healthy tissue, for example.

The marker compositions can also include certain enzymes. Enzymes are used in the debridement of both acute and chronic wounds. Debridement is the removal of nonviable tissue and foreign matter from a wound and is a naturally occurring event in the wound-repair process. During the inflammatory phase, neutrophils and macrophages digest and remove "used" platelets, cellular debris, and avascular injured tissue from the wound area. However, with the accumulation of significant amounts of damaged tissue, this natural process becomes overwhelmed and insufficient. Build-up of necrotic tissue then places considerable phagocytic demand on the wound and retards wound healing. Consequently, debridement of necrotic tissue is a particular objective of topical therapy and an important component of optimal wound management.

Enzymes, for example, may be incorporated into hydrogels of the present invention for topical application to provide a selective method of debridement. Suitable enzymes may be derived from various sources, such as krill, crab, *papaya*, bovine extract, and bacteria Commercially available, suitable enzymes include collagenase, papain/urea, and a fibrinolysin and deoxyribonuclease combination.

Enzymes for use in the present invention generally work in one of two ways: by directly digesting the components of slough (e.g., fibrin, bacteria, leukocytes, cell debris, serous exudate, DNA); or, by dissolving the collagen "anchors" that secure the avascular tissue to the underlying wound bed.

The marker of the present invention may be delivered by any suitable method, such as via a syringe or bellows pack (single dose delivery systems) or a multidose system, such as a pressurised delivery system or delivery via a 'bag in the can' type system (such as that published in WO98/32675). An example of a bellows pack is shown in published UK design number 2082665. The marker of the invention may also be delivered during surgery by direct placement (in the case of an open surgical procedure) or via a catheter during a closed surgical procedure.

Crosslinking

For certain applications, the polymers of the markers of the invention may be covalently crosslinked. The disclosure contemplates that crosslinking may be desired as between the polymers of the gel/hydrogel component, but also crosslinking may be desired as between the polymers of the gel/hydrogel and the MRI contrast agents and/or other active agent of the materials of the invention. The invention contemplates any suitable means for crosslinking polymers to one another, and crosslinking the gel/hydrogel polymers with the other components of the invention. The gel/hydrogel polymers may be covalently crosslinked to other polymers or to the nanostructures, either intramolecularly or intermolecularly or through covalent bonds. In the former case, there are no covalent bonds linking the polymers to one another or to the nanostructures, while in the latter case, there are covalent crosslinks binding the polymers to one another or to the nanostructures. The crosslinks may be formed using any suitable means, including using heat, radiation, or a chemical curing (crosslinking) agent. The degree of crosslinking should be sufficient to eliminate or at least minimize cold flow under compression.

For thermal crosslinking, a free radical polymerization initiator is used, and can be any of the known free radical-generating initiators conventionally used in vinyl polymerization. Preferred initiators are organic peroxides and azo compounds, generally used in an amount from about 0.01 wt. % to 15 wt. %, preferably 0.05 wt. % to 10 wt. %, more preferably from about 0.1 wt. % to about 5% and most preferably from about 0.5 wt. % to about 4 wt. % of the polymerizable material. Suitable organic peroxides include dialkyl peroxides such as t-butyl peroxide and 2,2bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo compounds include azo bis (isobutyronitrile) and azo bis (2,4-dimethylvaleronitrile). The temperature for thermally crosslinking will depend on the actual components and may be readily deduced by one of ordinary skill in the art, but typically ranges from about 80 C. to about 200 C.

Crosslinking may also be accomplished with radiation, typically in the presence of a photoinitiator. The radiation may be ultraviolet, alpha, beta, gamma, electron beam, and x-ray radiation, although ultraviolet radiation is preferred. Useful photosensitizers are triplet sensitizers of the "hydrogen abstraction" type, and include benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylaceto-phenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthonse such as 2-isopropylthioxanthone, 2-chlorothioxanthone, 2,4 dimethyl thioxanone, 2,4 dichlorothioxanone, and 2,4-diethyl thioxanone, and acyl phosphine oxides. Radiation having a wavelength of 200 to 800 nm, preferably, 200 to 500 nm, is preferred for use herein, and low intensity ultraviolet light is sufficient to induce crosslinking in most cases. However, with photosensitizers of the hydrogen abstraction type, higher intensity UV exposure may be necessary to achieve sufficient crosslinking. Such exposure can be provided by a mercury lamp processor such as those available from PPG, Fusion, Xenon, and others. Crosslinking may also be induced by irradiating with gamma radiation or an electron beam. Appropriate irradiation parameters, i.e., the type and dose of radiation used to effect crosslinking, will be apparent to those skilled in the art.

Suitable chemical curing agents, also referred to as chemical crosslinking "promoters," include, without limitation, polymercaptans such as 2,2-dimercapto diethylether, dipentaerythritol hexa(3-mercaptopropionate), ethylene bis(3-mercaptoacetate), pentaerythritol tetra(3-mercaptopropionate), pentaerythritol tetrathioglycolate, polyethylene glycol dimercaptoacetate, polyethylene glycol di(3-mercaptopropionate), trimethylolethane tri(3-mercaptopropionate), trimethylolethane trithioglycolate, trimethylolpropane tri(3-mercaptopropionate), trimethylolpropane trithioglycolate, dithioethane, di- or trithiopropane and 1,6-hexane dithiol. The crosslinking promoter is added to the uncrosslinked hydrophilic polymer to promote covalent crosslinking thereof, or to a blend of the uncrosslinked hydrophilic polymer and the complementary oligomer, to provide crosslinking between the two components.

The polymers and/or nanostructures may also be crosslinked prior to admixture with the complementary oligomer. In such a case, it may be preferred to synthesize the polymer in crosslinked form, by admixing a monomeric precursor to the polymer with multifunctional comonomer and copolymerizing. Examples of monomeric precursors and corresponding polymeric products are as follows: N-vinyl amide precursors for a poly(N-vinyl amide) product; N-alkylacrylamides for a poly(N-alkylacrylamide) product; acrylic acid for a polyacrylic acid product; methacrylic acid for a polymethacrylic acid product; acrylonitrile for a poly(acrylonitrile) product; and N-vinyl pyrrolidone (NVP) for a poly(vinylpyrrolidone) (PVP) product. Polymerization may be carried out in bulk, in suspension, in solution, or in an emulsion. Solution polymerization is preferred, and polar organic solvents such as ethyl acetate and lower alkanols (e.g., ethanol, isopropyl alcohol, etc.) are particularly preferred. For preparation of hydrophilic vinyl polymers, synthesis will typically take place via a free radical polymerization process in the presence of a free radical initiator as described above. The multifunctional comonomer include, for example, bisacrylamide, acrylic or methacrylic esters of diols such as butanediol and hexanediol (1,6-hexane diol diacrylate is preferred), other acrylates such as pentaerythritol tetraacrylate, and 1,2-ethylene glycol diacrylate, and 1,12-dodecanediol diacrylate. Other useful multifunctional crosslinking monomers include oligomeric and polymeric multifunctional (meth)acrylates, e.g., poly(ethylene oxide) diacrylate or poly(ethylene oxide) dimethacrylate; polyvinylic crosslinking agents such as substituted and unsubstituted divinylbenzene; and difunctional urethane acrylates such as EBECRYL 270 and EBECRYL 230 (1500 weight average molecular weight and 5000 weight average molecular weight acrylated urethanes, respectively—both available from UCB of Smyrna, Ga.), and combinations thereof. If a chemical crosslinking agent is employed, the amount used will preferably be such that the weight ratio of crosslinking agent to hydrophilic polymer is in the range of about 1:100 to 1:5. To achieve a higher crosslink density, if desired, chemical crosslinking is combined with radiation curing.

Other Modifications

The markers of the invention may be in any suitable form (e.g. wafer, disc, block, sphere) and contain additional physical modifications that may further assist the efficient attachment of the marker to a desired surgical site. Such means may include physical features, such as polymer nanospikes. Other means may include adhesives (biological). Still other means might include surface ligands or compounds (e.g., antibodies) that interact specifically with the target surgical site. Such means of modification will be well known in the art.

MRI Contrast Agent

The marker compositions also include an MRI contrast agent. The contrast agent can include Gadolinium or any other suitable contrast agent. As used herein, MRI contrast agents refer to a group of contrast media used to improve the visibility of internal body structures in magnetic resonance imaging (MRI). The most commonly used compounds for contrast enhancement are gadolinium-based. MRI contrast agents alter the relaxation times of atoms within body tissues where they are present after oral or intravenous administration. In MRI scanners sections of the body are exposed to a very strong magnetic field, then a radiofrequency pulse is applied causing some atoms (including those in contrast agents) to spin and then relax after the pulse stops. This relaxation emits energy which is detected by the scanner and is mathematically converted into an image. The MRI image can be weighted in different ways giving a higher or lower signal. The invention contemplates any suitable MRI-contrast agent, including gadoterate (Dotarem), gadodiamide (Omniscan), gadobenate (MultiHance), gadopentetate (Magnevist, Magnegita, Gado-MRT ratiopharm), gadoteridol (ProHance), gadoversetamide (OptiMARK), gadoxetate (Primovist), and gadobutrol (Gadovist).

Other MRI-contrast agents include iron oxide type. Two types of iron oxide contrast agents exist: superparamagnetic iron oxide (SPIO) and ultrasmall superparamagnetic iron oxide (USPIO). These contrast agents consist of suspended colloids of iron oxide nanoparticles and when injected during imaging reduce the T2 signals of absorbing tissues. SPIO and USPIO contrast agents have been used successfully in some instances for liver tumor enhancement. Although SPIOs and USPIOs have been approved for use in the past, it appears that all of the agents listed below are no longer available with the exception of the oral iron oxide contrast agent, Lumirem/Gastromark. Also, iron platinum agents are contemplated. Manganese-based agents can also be used.

Exemplary Embodiments

Reference will now be made to the drawings wherein like reference numerals identify similar structural features or aspects of the subject disclosure. For purposes of explanation and illustration, and not limitation, an illustrative view of an embodiment of a marker in accordance with the disclosure is shown in FIG. 1 and is designated generally by reference character 100. The systems and methods described herein can be used to mark an anatomical location without requiring surgical removal of markers or potential illness due to toxicity relating to non-dissolvable markers.

In at least one aspect of this disclosure, referring to FIG. 1, a marker 100 for imaging includes a bio-dissolvable material and a contrast agent configured to provide contrast during an imaging procedure (e.g., MRI). The bio-dissolvable material can include a polymer or any other suitable type of dissolvable material.

As shown in FIG. 1, the marker 100 can be wafer shaped or any other suitable shape (e.g., spherical, square, cubical).

In at least one aspect of this disclosure, a method can include forming a marker 100 as disclosed herein for imaging from a bio-dissolvable material and impregnating the bio-dissolvable material with a contrast agent. The method can further include shaping the marker 100 into a wafer shape. Any other suitable method of manufacture is contemplated herein. In at least one aspect of this disclosure, a method can include implanting a bio-dissolvable marker 100 for imaging into a patient.

In use, the marker 100 can be implanted after or during surgery at a site of interest. Later, a clinician can image the site of interest and easily locate such the site on the images by finding the marker 100. However, instead of requiring eventual removal of the marker 100 or risking toxicity or other health implications as a result of having the marker 100 in the patient's body, the marker 100 ultimately dissolves and is harmlessly absorbed.

Figure 2A:
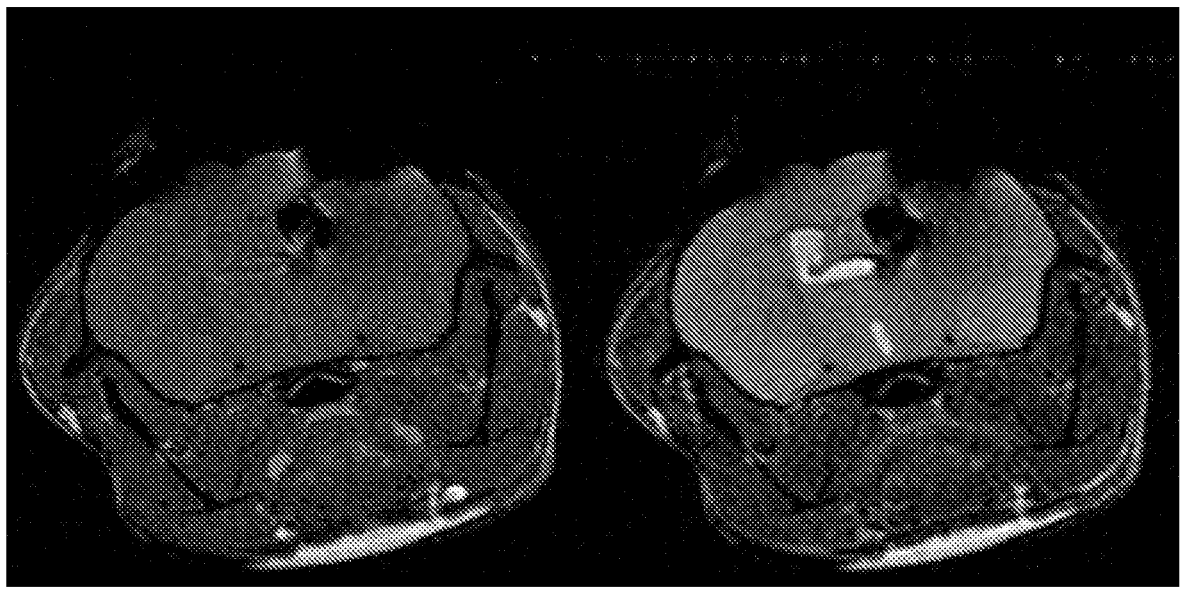
FIG. 2A shows a 1: T1 (left) and T2 (right) weighted axial slice of mouse tissue through the edge of the polymer impregnated with Gadolinium in accordance with this disclosure.
Figure 2B:
FIG. 2B shows T1 (left) and T2 (right) weighted axial slice of mouse tissue through the edge of the polymer impregnated with Gadolinium.

Referring to FIGS. 2A and 2B, a study was performed to determine the feasibility of a dissolvable wafer 100. The bio-dissolvable material was selected to be polifeprosan in a wafer shape and impregnated with the MRI contrast agent Gadolinium. Mice were then implanted with the wafer marker. As shown in FIG. 2A, the wafer successfully was picked up on MRI imaging post-implantation on Day 1. Moreover, results on Day 17 (shown in FIG. 2B) demonstrate durability of wafer marking.

The methods and systems of the present disclosure, as described above and shown in the drawings, provide for improved markers for post-surgical imaging with superior properties including bio-dissolvability. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A marker for imaging, comprising:
   a bio-dissolvable material including a hydrophilic polymer; and
   a contrast agent configured to provide contrast during an imaging procedure, the contrast agent comprising Gadolinium,
   wherein the hydrophilic polymer of the bio-dissolvable material is impregnated with and covalently crosslinked to the Gadolinium.

2. The marker of claim 1, wherein the marker is wafer shaped.

3. A method, including:
   forming a marker for imaging from a bio-dissolvable material including a hydrophilic polymer;
   impregnating the hydrophilic polymer of the bio-dissolvable material with a contrast agent, the contrast agent comprising Gadolinium; and
   covalently crosslinking the hydrophilic polymer of the bio-dissolvable material to the Gadolinium.

4. The method of claim 3, further comprising shaping the marker into a wafer shape.

5. The method of claim 3, further comprising:
   implanting the marker into a patient.

6. The method of claim 3, wherein the hydrophilic polymer of the bio-dissolvable material further comprises a cellulose ester.

7. The method of claim 3, wherein the hydrophilic polymer of the bio-dissolvable material further comprises cellulose acetate, cellulose acetate propionate, cellulose acetate butyrate, cellulose propionate, cellulose butyrate, cellulose propionate butyrate, cellulose diacetate, and/or cellulose triacetate.

8. The method of claim 3, wherein the hydrophilic polymer of the bio-dissolvable material further comprises an acrylate polymer.

9. The method of claim 8, wherein the acrylate polymer comprises polymerized units of acrylic acid, methacrylic acid, methyl acrylate, ethyl acrylate, methyl methacrylate, and/or ethyl methacrylate.

10. The marker of claim 1, wherein the bio-dissolvable material comprises polifeprosan which is impregnated with and covalently crosslinked to the Gadolinium.

11. The marker of claim 10, further comprising a nitrosourea alkylating agent, the release of which is controlled by the polifeprosan.

12. The marker of claim 10, wherein the polifeprosan forms a hydrogel.

13. The marker of claim 12, wherein the hydrogel contains an active agent to be released upon dissolution of the hydrogel.

14. The marker of claim 12, wherein the hydrogel comprises hyaluronic acid (HA).

15. The marker of claim 12, wherein the hydrogel comprises epidermal growth factor (EDF), platelet-derived growth factor (PDGF), or nerve growth factor (NGF).

16. The marker of claim 12, wherein the hydrogel comprises an enzyme for wound debridement.

17. The marker of claim 13, wherein the hydrogel is covalently crosslinked to the Gadolinium and the active agent.

18. The marker of claim 12, wherein including the nitrosourea alkylating agent is carmustine.

19. A marker for imaging, comprising:
    a bio-dissolvable material including a hydrophilic polymer; and
    a contrast agent configured to provide contrast during an imaging procedure, the contrast agent comprising Gadolinium,
    wherein the bio-dissolvable material comprises polifeprosan which is impregnated with and covalently crosslinked to the Gadolinium.

20. The marker of claim 19, further comprising a nitrosourea alkylating agent, the release of which is controlled by the polifeprosan.

21. The marker of claim 19, wherein the polifeprosan forms a hydrogel.

* * * * *